United States Patent
Frey, II

(10) Patent No.: US 9,821,149 B2
(45) Date of Patent: Nov. 21, 2017

(54) METHODS FOR USING ULTRASOUND FOR ENHANCING EFFICIENCY AND TARGETING OF INTRANASAL ADMINISTRATION OF THERAPEUTIC COMPOUNDS TO THE CENTRAL NERVOUS SYSTEM

(71) Applicant: HealthPartners Research & Education, Bloomington, MN (US)

(72) Inventor: William H. Frey, II, White Bear Lake, MN (US)

(73) Assignee: HealthPartners Research & Education, Minneapolis, MN (US)

( * ) Notice: Subject to any disclaimer, the term of this patent is extended or adjusted under 35 U.S.C. 154(b) by 116 days.

(21) Appl. No.: 13/650,344

(22) Filed: Oct. 12, 2012

(65) Prior Publication Data
US 2013/0096488 A1  Apr. 18, 2013

Related U.S. Application Data

(60) Provisional application No. 61/547,119, filed on Oct. 14, 2011.

(51) Int. Cl.
*A61M 37/00* (2006.01)
*A61K 41/00* (2006.01)
*A61K 9/00* (2006.01)
*A61K 9/127* (2006.01)

(52) U.S. Cl.
CPC ....... *A61M 37/0092* (2013.01); *A61K 9/0043* (2013.01); *A61K 9/127* (2013.01); *A61K 41/0047* (2013.01)

(58) Field of Classification Search
CPC .......................... A61K 9/0043; A61M 37/0092
USPC ..................................... 604/19, 23
See application file for complete search history.

(56) References Cited

U.S. PATENT DOCUMENTS

| | | | |
|---|---|---|---|
| 5,725,515 A | 5/1998 | Jolesz et al. | |
| 8,545,405 B2 * | 10/2013 | Raghavan | A61M 37/00 600/437 |
| 2007/0265203 A1 * | 11/2007 | Eriksson et al. | 514/12 |
| 2009/0005711 A1 | 1/2009 | Konofagou et al. | |
| 2009/0068155 A1 * | 3/2009 | Frey, II et al. | 424/93.7 |
| 2012/0109045 A1 * | 5/2012 | Wrenn et al. | 604/22 |

FOREIGN PATENT DOCUMENTS

WO   WO 2010123918   * 10/2010

OTHER PUBLICATIONS

Mitragotri, "Healing sound: the use of ultrasound in drug delivery and other therapeutic applications", Nature Reviews Drug Discovery 4, 255-260 (Mar. 2005).*
Pitt et al., "Ultrasonic Drug Delivery—A General Review", Expert Opin Drug Deliv. Nov. 2004; 1(1): 37-56.*
Choi et al: "Noninvasive and localized neuronal delivery using short ultrasonic pulses and microbubbles", Edited by Robert Langer, Massachusetts Institute of Technology, Cambridge, MA, and approved Aug. 9, 2011 (received fro review Mar. 31, 2011).

* cited by examiner

*Primary Examiner* — Matthew F Desanto
(74) *Attorney, Agent, or Firm* — Barnes & Thornburg LLP; Jeffrey R. Stone

(57) ABSTRACT

The present invention is directed to methods for reducing systemic absorption of therapeutic compounds or agents while enhancing efficiency of delivery and targeting of intranasal administration of such compounds or agents to the central nervous system. More specifically, use of ultrasound technology in conjunction with intranasal delivery of a therapeutic compound, or pharmaceutical composition, wherein the intranasal delivery is preferably to the upper one third of a patient's nasal cavity, thereby reducing therapeutic compound or agent absorption into the blood. At the same time, the present invention results in reducing the delivery of therapeutic compounds and/or agents to the peripheral tissues, increases therapeutic delivery of the compounds and/or agents to the central nervous system generally, and increases targeting of the therapeutics and/or agents to specific target regions within the central nervous system.

8 Claims, No Drawings

METHODS FOR USING ULTRASOUND FOR ENHANCING EFFICIENCY AND TARGETING OF INTRANASAL ADMINISTRATION OF THERAPEUTIC COMPOUNDS TO THE CENTRAL NERVOUS SYSTEM

CROSS-REFERENCE TO RELATED APPLICATIONS

The present application claims priority to provisional application Ser. No. 61/547,119, filed on Oct. 14, 2011, entitled "Enhancement Of Intranasal Delivery of Therapeutics Directly To The CNS Using Ultrasound Technology", the entire contents of which are hereby incorporated by reference.

FEDERAL FUNDING

None

BACKGROUND OF THE INVENTION

Field of the Invention

The present invention is directed to methods for reducing systemic absorption of therapeutic compounds or agents while enhancing efficiency of delivery and targeting of intranasal administration of such compounds or agents to the central nervous system generally and preferentially to one or more specific regions of the central nervous system. More specifically, use of ultrasound technology in conjunction with intranasal delivery of a therapeutic compound, or pharmaceutical composition, wherein the intranasal delivery is preferably to the upper one third of a patient's nasal cavity, thereby reducing therapeutic compound or agent absorption into the blood while targeting the therapeutic compound to one or more specific regions of the central nervous system.

Description of the Related Art

It is known that intranasal administration of therapeutic compounds or agents may, in some cases, increase the effectiveness of certain therapeutic compounds or agents in bypassing the blood-brain barrier (BBB) and delivering the compound or agent directly to the Central Nervous System (CNS). Thus, intranasal administration of therapeutic compounds may allow increased prevention and/or treatment of certain diseases or conditions.

Intranasal delivery, preferably to the upper third of a patient's nasal cavity, is a means of bypassing the BBB to administer therapeutic compounds and/or agents directly to the CNS. Evidence exists that intranasal treatment improves, i.e., prevents and/or treats, a variety of neurological and psychiatric disorders, e.g., stroke, in animals. When delivered to the upper third of the patient's nasal cavity, the vast majority of many administered therapeutic compounds and/or agents which reach the CNS from the nasal mucosa, bypass the BBB. This basic methodology is discussed and described in U.S. Pat. No. 5,624,898 to Frey II entitled Method for Administering Neurologic Agents to the Brain, the entire contents of which are hereby incorporated by reference. This intranasal administration technique is a vast improvement over systemic administration methods such as intravenous and oral administration of drugs which generally cannot cross the BBB to reach their targets within the CNS. In addition, Frey's intranasal method is a significant improvement over the general inhalation methods which target the lower two-thirds of the patient's nasal cavity. Both the systemic and general intranasal method targeting the lower two-thirds of the nasal cavity result in a very large, unwanted and potentially dangerous systemic exposure to the administered drug or therapeutic. The present invention addresses, inter alia, this general intranasal problem as well as improves the efficiency of Frey's upper one-third intranasal administration and improves the targeting of therapeutics to specific areas of the CNS.

General inhalation methods to the lower two-thirds of the nasal cavity delivered by, e.g., nasal spray bottles, on the other hand, result in a large amount of systemic absorption and exposure, with a very small amount, i.e., less than 5%, making the tortuous journey around the turbinates to the upper third of the nasal cavity and further bypassing the BBB to reach the CNS. The present invention can improve even this inefficient procedure by using focused ultrasound energy to improve the delivery efficiency to the CNS generally as well as providing a focused delivery to at least one target region within the CNS Intranasal delivery of therapeutic compounds, both to the patient's nasal cavity generally with the majority of the administered compound(s) delivered to the lower two-thirds of the nasal cavity, and to the upper third of the nasal cavity specifically, comprise known procedures. Delivery and administration to the upper third of the nasal cavity, is very effective in administering the subject compounds or agents to the desired target, i.e., the CNS, without significant systemic exposure, though some systemic exposure does occur as is further discussed below. The present invention uses focused ultrasound energy to improve the delivery efficiency of intranasal delivery administration techniques to the CNS generally as well as providing a focused delivery to at least one target region within the CNS, as opposed to non-target systemic organs and other body parts.

Unwanted systemic exposure of therapeutics used to treat CNS diseases create several problems. The systemic metabolism greatly reduces the bioavailability of any agent and/or compound exposed to the non-CNS system. This reduction of bioavailability is increased by unwanted plasma protein binding of the agent and/or compound. As a result, only a small amount of the active therapeutic agent and/or compound actually reaches the CNS. Because of these, inter alia, issues, the actual dose that must be administered in order to achieve a therapeutic dose in the targeted CNS is far larger than the therapeutic dosing. As a consequence, a relatively large concentration of the agent(s) and/or compounds(s) is in the system and will affect non-target systemic organs and systems. This can create unwanted and often dangerous side effects on these non-target organs and systems.

We have addressed the efficiency needs in patent application Ser. No. 12/134,385 to Frey II, et al., entitled "Pharmaceutical Compositions and Methods for Enhancing Targeting of Therapeutic Compounds to the Central Nervous System, the entire contents of which are hereby incorporated by reference, and wherein a vasoconstrictor is administered to the patient's nasal cavity either just prior to, or in combination with, administration of a pharmaceutical composition comprising a therapeutic compound(s) and/or agent (s). The efficiency of the direct administration of the pharmaceutical compound to the CNS, with concomitant reduction of systemic exposure of the pharmaceutical compound is remarkable.

However, we have also determined that at times very high concentrations of an intranasally administered therapeutic compound and/or agent are found in the system. For example, in Dhuria et al. (2009) JPET 328(1):312-320, we report that very high concentrations of intranasally administered drug are found in the walls of the carotid artery (83 nM) relative to the blood (3.4 nM) and brain (approximately 1 nM). In the presence of a vasoconstrictor in the formulation, there is an even higher concentration of drug in the walls of the carotid relative to the blood or brain. Similarly, in the walls of the basilar artery and circle of willis blood vessels, there are higher concentrations of drug following intranasal delivery than in the blood or brain as reported by Thorne et al. (2004) Neurosci. 127:481-496. It is known that intranasal drugs and/or therapeutics distribute throughout the CNS through the perivascular spaces of blood vessels of the cerebrovasculature once they reach the CNS by traveling along the olfactory and trigeminal neural pathways. The present invention can aid in moving these intranasally delivered therapeutic agents and/or compounds from the perivascular spaces to the targeted CNS region(s) where the ultrasound is focused. This is in addition to the present invention's utility in moving bloodstream-borne therapeutic agent(s) and/or compound(s) from the bloodstream through the BBB to one or more ultrasonic-energy targeted CNS regions. In addition, the concentration of the therapeutic agent and/or compound is increased at the target region(s) of the CNS where the ultrasound energy is focused.

Therefore, even the most efficient of the known intranasal delivery systems and methods are subject to efficiency improvements. In particular, therapeutic compounds may be absorbed into the blood and/or delivered to peripheral (non-target) tissues, thus reducing delivery of the compound to the target. It would be desirable to reduce absorption of therapeutic compounds or agents into the blood and delivery to non-target or peripheral tissues not located in the CNS.

Thus, it would be desirable to increase the efficiency of uptake of agents and/or compounds into the CNS using general intranasal administration techniques wherein the therapeutic agent and/or compound is administered primarily to the lower two-thirds of the patient's nasal cavity.

It would be further desirable to increase the efficiency of uptake of agents and/or compounds into the CNS using intranasal administration techniques wherein the therapeutic agent and/or compound is administered primarily to the upper one third of the patient's nasal cavity.

It would be still further desirable to increase the targeting ability within the CNS for therapeutic agent(s) and/or compound(s) delivered either by general inhalation methods, i.e., to the lower two-thirds of the nasal cavity, or by delivering the agent(s) and/or compound(s) directly to the CNS by administration to the upper one third of the patient's nasal cavity.

Given the situation described above there is a need for, inter alia: increasing efficiency of intranasal administration of therapeutic compounds and/or agents to the CNS; increased targeting of intranasal delivery of therapeutic compounds and/or agents to target regions within the CNS; and decreasing absorption of the intranasally administered therapeutic compounds and/or agents to the blood and peripheral tissues. The present invention addresses these, among other, needs.

BRIEF SUMMARY OF THE INVENTION

The present invention is directed to methods for reducing systemic absorption of therapeutic compounds or agents while enhancing efficiency of delivery and targeting of intranasal administration of such compounds or agents to the central nervous system and preferentially to one or more specific brain regions. More specifically, use of ultrasound technology in conjunction with intranasal delivery of a therapeutic compound, or pharmaceutical composition, wherein the intranasal delivery is preferably to the upper one third of a patient's nasal cavity, thereby reducing therapeutic compound or agent absorption into the blood. At the same time, the present invention results in reducing the delivery of therapeutic compounds and/or agents to the peripheral tissues, increases therapeutic delivery of the compounds and/or agents to the central nervous system generally, and increases targeting of the therapeutics and/or agents to specific target regions within the central nervous system.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying Figures and Tables included herein.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Definitions

As used herein, "central nervous system" (CNS) refers to the brain and spinal cord and associated tissues.

As used herein, "drug targeting" refers to increasing drug concentration in a tissue relative to the concentration of that drug in the blood.

An "effective amount" of therapeutic compound or agent is an amount sufficient to prevent, treat, reduce and/or ameliorate the symptoms, neuronal damage and/or underlying causes of any of the referenced disorders or diseases. In some instances, an "effective amount" is sufficient to eliminate the symptoms of those diseases and, perhaps, overcome the disease itself.

In the context of the present invention, the terms "treat" and "therapy" and "therapeutic" and the like refer to alleviate, slow the progression, prophylaxis, attenuation or cure of cerebral ischemia or neurodegeneration or other CNS-related disease and/or condition.

"Prevent", as used herein, refers to putting off, delaying, slowing, inhibiting, or otherwise stopping, reducing or ameliorating the onset of cerebral ischemia or neurodegeneration or other CNS-related disease and/or condition. It is preferred that a large enough quantity of the agent be applied in non-toxic levels in order to provide an effective level of neuroprotection. The method of the present invention may be used with any animal, such as a mammal or a bird (avian), more preferably a mammal. Poultry are a preferred bird. Exemplary mammals include, but are not limited to rats, cats, dogs, horses, cows, sheep, pigs, and more preferably humans.

The method of the present invention delivers the therapeutic agent and/or compound to the nasal cavity of a mammal for direct delivery to the CNS. It is preferred that the agent and/or compound be administered to the olfactory neuroepithelium in the upper one third of the nasal cavity in order to promote rapid and efficient delivery of the agent to the CNS along the olfactory neural pathway and to the respiratory and olfactory epithelium to promote rapid and efficient delivery of the agent to the CNS along the trigeminal neural pathway rather than into the capillaries within the nasal epithelium. Transport of the therapeutic agent to the brain by means of the olfactory and trigeminal neural pathways rather than the circulatory system is preferred so that harmful systemic side effects and potentially short half-life of the therapeutic agent in the blood are avoided. Further, certain agents may simply be unable due to size to cross the BBB from the bloodstream into the CNS. The preferred method allows direct delivery of such molecules to the CNS and to the dura mater and lymphatics.

An alternate embodiment of the present invention comprises administration of the therapeutic agent and/or compound to the lower two-thirds of the nasal cavity using, e.g., nasal spray bottles and the equivalent.

Thus, in the preferred intranasal administration, to deliver the therapeutic compound(s) or agent(s) to the CNS, the compound(s) or agent(s) in combination with at least one vasoconstrictor as a pharmaceutical composition may be administered to respiratory epithelium of the nasal cavity or to the olfactory epithelium located in the upper one-third of the nasal cavity. The composition may be administered intranasally as a powder or liquid spray, nose drops, a gel, lipid emulsion, lipid nanoparticles, lipid nanospheres or ointment, through a tube or catheter, by syringe, packtail, pledget or by submucosal infusion. Optimization of the administration of the therapeutic agent is provided by the various embodiments by applying the agent to the mucosa and/or epithelium of the nasal cavity.

The optimal concentration of the active therapeutic agent and/or compound will necessarily depend upon the specific neurologic agent used, the characteristics of the patient and the nature of the disease or condition for which the agent is being used, though an effective amount is contemplated. In addition, the concentration will depend upon whether the agent is being employed in a preventive or treatment capacity. Further, the stage of a particular disease or disorder, e.g., early vs. late Alzheimer's disease, may dictate the optimal concentration of the agent and/or compound.

The present invention enhances the efficiency and/or targeting of intranasal administration of therapeutic compound(s) and/or agent(s) to the CNS, and specific regions within the CNS, by incorporating BBB-disrupting, or alternatively, BBB hole-creating, ultrasound technology following the intranasal administration. Thus, intranasal delivery of a therapeutic compound(s) or agent(s) in combination with focused ultrasound energy enhances the efficiency of delivery of therapeutic agents and/or compounds by intranasal administration to the CNS and targeting specific regions within the CNS by using focused ultrasound on the specific region(s) for the agents and/or compounds.

Intranasal delivery is a novel method to target drugs to the CNS for the treatment of neurologic and psychiatric diseases and disorders. While numerous studies demonstrate that a wide variety of therapeutic agents and/or compounds rapidly reach the brain and spinal cord and have beneficial effects in animals and in humans after intranasal administration, few research efforts have been made to improve intranasal drug targeting to the CNS. In the present invention, we present a novel strategy to enhance both the efficiency of delivery of intranasal delivery of therapeutic agents and/or compounds to the CNS as well as provide a mechanism for targeting the intranasally delivered drugs to specific regions within the CNS by incorporating focused ultrasound technology targeted at the CNS region where the drug is needed and desired following the intranasal administration step. Thus, in comparison with simple intranasal delivery (either targeting the upper one-third or lower two-thirds of the nasal cavity) of a drug or therapeutic agent and/or compound to the CNS, the use of focused ultrasound energy aimed at one or more target regions of the CNS following intranasal administration of the drug will increase delivery and targeting to those specific regions of the CNS as compared to other regions of the CNS.

Moreover, we provide disclosure of the following patents and applications, each of which are commonly assigned with the present application and incorporated herein in their entirety for disclosure of, inter alia, the various diseases, conditions or disorders of the CNS, as well as various compounds and/or therapeutic agents for treating same by application to the upper ⅓ of the nasal cavity:

U.S. Pat. No. 7,972,595 Methods and compositions for protecting and treating at least one muscarinic receptor from dysfunction not resulting from oxidative stress, toxic actions of metals or infectious agents by administering a pyrophosphate analog;

U.S. Pat. No. 7,786,166 Methods and compositions for protecting and treating muscarinic receptors through administration of at least one protective agent;

U.S. Pat. No. 7,776,312 Method of treating Alzheimer's disease comprising administering deferoxamine (DFO) to the upper one-third of the nasal cavity;

U.S. Pat. No. 7,618,615 Methods for providing neuroprotection for the animal central nervous system against neurodegeneration caused by ischemia;

U.S. Pat. No. 7,084,126 Methods and compositions for enhancing cellular function through protection of tissue components;

U.S. Pat. No. 6,313,093 Method for Administering Insulin to the Brain;

US Pat Application 20100061959 Methods for Providing Neuroprotecton for the Animal Central Nervous System Against the Effects of Ischemia, Neurodegeneration, Trauma, and Metal Poisoning;

US Patent Application 20080305077 Pharmaceutical Compositions and Method for Enhancing Targeting of Therapeutic Compounds to the Central Nervous System;

US Patent Application 20110311654 Methods and Pharmaceutical Compositions for Treating the Animal Central Nervous System for Psychiatric Disorders;

US Patent Application 20110236365 Method for Protecting and Treating at Least One Muscarinic Receptor From Dysfunction Resulting From Free Radical Damage.

In addition, it is understood that general inhalation, i.e., administration to the lower two-thirds, of the disclosed therapeutic agents and/or compounds and/or pharmaceutical compositions in the above incorporated references for the treatment and/or prevention of the disclosed diseases and/or conditions is also an element of certain embodiments of the present invention.

Generally, use of ultrasound technology for delivery of compounds, agents and/or molecules and the like through the BBB has been known for years. For example, U.S. Pat. No. 5,752,515 to Julesz and entitled "Methods and Apparatus for Image-Guided Ultrasound Delivery of Compounds Through the Blood-Brain Barrier, the entire contents of which are hereby incorporated by reference, describes using ultrasound delivery of compounds through the BBB to selected location in the brain target. Julesz comprises systemic, i.e., IV or oral, administration of the therapeutic compound and/or agent to the subject patient. Stated differently, Julesz teaches delivery of a compound into the patient's bloodstream. Subsequently, Julesz uses application of ultrasound energy to open a hole, or holes, in the BBB, to allow delivery of some of the circulating compound from the patient's bloodstream into the patient's CNS, specifically the brain. This is a relatively primitive way to achieve delivery of a therapeutic dose into the patient's CNS. As discussed above, systemic administration requires potentially harmful overdosing to the bloodstream in order to achieve the desired therapeutic dose within the CNS. In addition, Julesz teaches creating holes, which later heal or close, in the BBB. One major problem and drawback is the potential for hemorrhage.

Subsequent refinements and modifications to the teachings of Julesz are found in US patent application 20090005711 to Konofagou, entitled "Systems and Methods For Opening Of The Blood-Brain Barrier Of A Subject Using Ultrasound", the entire contents of which are also hereby incorporated by reference. In this application, Konofagou describes targeting a region of the brain for opening, following by application of a focused ultrasound beam through the skull of the subject to the targeted region of the brain in order to open the BBB. As with Julesz, however, the therapeutic compound is introduced systemically, i.e., via IV catheters or needles, followed by opening of the BBB with a focused ultrasound procedure. The problems associated with Julesz described supra are not addressed by Konofagou's '5711 application.

A further refinement of the use of ultrasound energy to assist compounds, agents and/or molecules to cross the BBB is found in the following article: Choi, James J., et al., "Noninvasive and localized neuronal delivery using short ultrasonic pulses and microbubbles", published in the online Early Edition of the *Proceedings of the National Academy of Sciences* the week of Sep. 19, 2011, the entire contents of which are also hereby incorporated by reference. This article describes using biologically inert and preformed microbubbles that are systemically, i.e., via IV or oral administration to the patient's bloodstream, and subsequently exposed to noninvasive short ultrasonic pulse energy. As described by the authors, the microbubbles respond to the short ultrasonic pulsing by becoming acoustically activated into acoustic cavitation. Thus, the cavitating microbubbles expand and contract with the acoustic pressure rarefaction and compression. In this technique, a subsisting hole is not created in the BBB, instead, the cavitation creates a disruption in the BBB, through which the microbubbles may pass from the patient's bloodstream into a targeted region of the CNS corresponding with the focused target of the ultrasonic energy.

The present invention may make use of the ultrasonic methods and techniques described by Julesz, Konofagou and/or Choi. If employing the methods described by Julesz and/or Konofagou, an effective dose of the therapeutic agent and/or compound may be administered intransally to the patient.

If the effective dose is administered to the upper one third of the patient's nasal cavity, most of the effective dose will reach the patient's CNS by, as described above, bypassing the BBB. However, as also discussed above, some small amounts of the effective dose will reach the patient's bloodstream.

If the effective dose is administered to the lower two-thirds of the patient's nasal cavity, most of the effective dose will be absorbed into the patient's bloodstream, with a very small amount actually reaching the CNS.

In both aforementioned cases, focused ultrasound energy may be used to enhance the efficiency of delivery of the administered effective dose to the CNS, by increasing movement of that portion of the effective dose absorbed into the patient's bloodstream through the BBB of the cerebrovasculature in the area where the ultrasound energy is focused and into the parenchymal tissues of the CNS. Further, in these cases, focused ultrasound energy may be used to enhance the efficiency of delivery and targeting of the effective dose to the CNS and to one or more specific regions of the CNS by increasing movement of the drug from the perivascular spaces of the cerebrovasculature into the parenchymal tissues of the CNS. Thus, the efficiency of delivery and targeting of the therapeutic agent and/or compound to the CNS is ultimately increased or enhanced as at least some of the bloodstream-borne agent and/or compound is transported through the BBB and that portion of the drug that reached the perivascular spaces of the cerebrovasculature of the CNS more easily enters the parenchymal tissues of the CNS in the specific regions where the ultrasound energy is focused.

In any of the embodiments described herein, the inventive method and system requires waiting for a time period after intranasal administration of the therapeutic agent and/or compound. This allows any of the agent and/or compound that was absorbed into the patient's bloodstream to circulate before being urged through the BBB by ultrasonic energy. The time period may range from 2 minutes to 120 minutes. More preferably, the time period range may be 5 minutes to 60 minutes.

If employing Choi's methods, the therapeutic agent and/ or compound may be encapsulated within biologically inert microbubbles as described. The microbubbles may then be administered intranasally to the patient. The techniques of opening holes in the BBB described by Julesz and/or Konofagou may then be used to create a passage through the BBB into the CNS, for that portion of the effective dose that was absorbed by the patient's bloodstream. Alternatively, Choi's noninvasive short ultrasonic pulse energy technique may be used to acoustically activate the microbubbles, and the therapeutic agent and/or compound encapsulated therein, into acoustic cavitation. Thus, the cavitating microbubbles expand and contract with the acoustic pressure rarefaction and compression. In this technique, a subsisting hole is not created in the BBB, instead, the cavitation creates a disruption in the BBB, through which the microbubbles may pass from the patient's bloodstream into a targeted region of the CNS corresponding with the focused target of the ultrasonic energy.

In all cases, regardless of the intranasal administration method or ultrasonic technique employed, the present invention comprising intranasal administration of a therapeutic agent and/or compound followed by focused ultrasonic disruption of the BBB, allows the agent and/or compound to be targeted to the region of the CNS where the ultrasonic energy disrupts the BBB. Thus, not only is an enhanced efficiency of delivery to the CNS achieved by the present invention, but the delivery is also targeted.

Several CNS-related disorders, diseases and/or conditions may be prevented, or the effects minimized, using different embodiments of the inventive method. For example, and without limitation, patients at risk for Alzheimer's disease may be aided by the technique.

Further, in another embodiment, those patients scheduled for coronary artery bypass graft (CABG) surgery may also benefit due to the relatively high percentage of post-surgical cerebral ischemia.

In another embodiment, patients at risk for Parkinson's disease may benefit from the inventive method.

In yet another embodiment, patients at risk for stroke may be aided by the inventive method. Such patients would include those having risk factors comprising hypertension, diabetes, obesity, smoking, antiphospholipid syndrome or with a history of stroke (thus prone to subsequent stroke).

The above embodiments essentially focus on prevention of the cognitive, behavioral and physical impairment due to cerebral ischemia as a result of certain disorders or medical procedures. A series of alternate embodiments focus on treating such disorders after they have been diagnosed.

For example, again without limitation, in one embodiment, the inventive method may be used in a treatment plan for patients with Alzheimer's disease.

In another embodiment, the inventive method may be used to treat patients diagnosed with Parkinson's disease.

In yet another embodiment, patients diagnosed with stroke, and thus at risk for a subsequent stroke, may benefit from the inventive method.

In yet another embodiment, the inventive method may be used to treat patients diagnosed with narcolepsy.

In another embodiment, the inventive method may be used to treat patients with social communication disorder, attention deficit disorder, autism and related conditions.

In another embodiment, the inventive method may be used to prevent and/or treat patients with, or at risk for, post-traumatic disorder (PTSD).

In yet another embodiment, the inventive method may be used to treat patients diagnosed with other disorders of the nervous system including: neurodegenerative disorders such as ALS and Huntington's disease, traumatic brain injury, spinal cord injury, epilepsy, hemorrhage, transient ischemic attacks, pain, depression, anxiety, schizophrenia, post-traumatic stress disorder, personality disorder, autism, eating disorders, and other psychiatric or neurologic disorders.

In one embodiment, a pharmaceutical composition may be comprised of at least one therapeutic compound and/or agent which is administered intransally, followed by targeted ultrasonic disruption of the BBB. Alternatively, the pharmaceutical composition may be encapsulated within a biologically inert microbubble.

In another embodiment, a pharmaceutical composition may be comprised of a combination of at least one therapeutic compound and/or agent and at least one vasoconstrictor which is administered intranasally, followed by targeted ultrasonic disruption of the BBB. Alternatively, the pharmaceutical composition may be encapsulated within a biologically inert microbubble.

In general, any of the therapeutic agents or pharmaceutical compositions described or referenced herein may be administered to under embodiments of the inventive method prior to a surgical procedure such as CABG, during such a procedure or after such a procedure.

In still another embodiment, the therapeutic agent and/or compound according to the inventive methods may comprise one or more of the following substances which stimulate and/or stabilize HIF-1α such as deferoxamine. Further therapeutic agents may comprise growth factors and neurotrophic factors such as insulin, IGF-I, heregulin insulin, IGF-I, NGF, BDNF, GDNF, FGF, heregulin, TGFbeta, TNFalpha and TGFbeta. It is within the scope of invention to create a pharmaceutical composition combining one or more of the foregoing substances with at least one vasoconstrictor. In addition, in other embodiments, the invention may administer a pharmaceutical composition comprising at least one of the foregoing substances with at least one metal chelator and at least one vasoconstrictor. Further, a pharmaceutical composition may be comprised in another embodiment of at least one of the foregoing substances combined with at least one antioxidant and at least one vasoconstrictor. In either of these embodiments, the therapeutic agent and/or compound or pharmaceutical composition may be encapsulated within a microbubble.

An effective amount, as herein defined, of the therapeutic agent to be administered pursuant to embodiments of the invention is the most preferred method of expression of dosage. Such effective amount is dependent upon many factors, including but not limited to, the type of disease or condition giving rise to an anticipated cerebral ischemic episode, the patient's general health, size, age, and the nature of treatment, i.e., short-term of chronic treatment. For illustrative purposes only, exemplary treatment regimens relating generally to the therapeutic agents disclosed herein, including dosage ranges, volumes and frequency are provided below:

Efficacious dosage range: 0.0001-1.0 mg/kg.
A more preferred dosage range may be 0.005-1.0 mg/kg.
The most preferred dosage range may be 0.05-1.0 mg/kg.
The dosage volume (applicable to nasal sprays or drops) range may be 0.015 mls-1.0 mls.
The preferred dosage volume (applicable to nasal sprays or drops) range may be 0.03-0.6 mls.
The efficacious vasoconstrictor dosage may be 0.0001-0.3 mg/kg.

Generally, the treatment may be given in a single dose or multiple administrations, i.e., once, twice, three or more times daily over a period of time. For chronic disorders such as those diagnosed with, or at risk for, Alzheimer's disease, stroke or Parkinson's disease, the treatment may consist of at least one dose per day over an extended period of time. Alternatively, for those patients anticipating CABG surgery, the treatment may be a one-time dose to precondition the CNS in anticipation of potential cerebral ischemia. Such preconditioning may require more than one dose and may be administered from 12 hours to 1 week prior to the CABG surgery.

The brain concentrations that are likely to be achieved with the dosage ranges provided above are, for a single dose: 0.1 nM-50 µM. Over the course of a multi-dose treatment plan, the maximum brain concentration may be as high as 500 µM.

An exemplary method of the invention may comprise:

1. A method for transporting an effective dose of at least one therapeutic agent and/or compound to a damaged or degenerating or injured central nervous system of a mammal, wherein the damage or degeneration or injury is caused by a neurological disease or condition or trauma within at least one region of the central nervous system, comprising:
administering the effective dose to the nasal cavity of the mammal;
enabling at least some of the at least one therapeutic agent and/or compound of the effective dose to directly access the damaged or degenerating or injured central nervous system by bypassing the BBB of the mammal, wherein at least a portion of the at least one therapeutic agent and/or compound of the effective dose enters the mammal's bloodstream;
allowing a time period to pass;

after passage of the time period, focusing ultrasound energy on at least one selected target region corresponding to the at least one central nervous system region that is damaged or degenerating or injured in order to disrupt the BBB; and enabling at least some of the portion of the at least one therapeutic agent and/or compound within the mammal's bloodstream to access the damaged central nervous system through the disrupted BBB at the at least one central nervous system region that is damaged or degenerating or injured.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A method for efficiently transporting an effective dose comprising at least one therapeutic agent to a targeted specific region of a damaged or degenerating or injured central nervous system of a mammal, wherein the damage or degeneration or injury is at least partially located within the targeted specific region and is caused by a neurological disease or condition or trauma within at least one region within the central nervous system, comprising:

administering at least an effective dose to the upper third of the nasal cavity of the mammal, thereby ensuring that at least an effective dose of the at least one therapeutic agent is enabled to directly access the patient's central nervous system by bypassing the blood-brain barrier of the mammal, while minimizing systemic exposure to the administered therapeutic agent;

following the administration and delivery of the at least an effective dose of the at least one therapeutic agent to the patient's central nervous system, focusing ultrasound energy on the targeted specific region within the mammal's central nervous system to drive the previously administered and delivered therapeutic agent from the perivascular space of the central nervous system to the parenchymal tissue of the targeted specific region;

transporting and delivering an effective dose of the therapeutic agent from the perivascular space to the parenchymal tissue of the targeted specific region;

treating the damaged or deteriorating or injured region of the central nervous system with the effective dose of the at least one therapeutic agent while minimizing exposure of non-targeted regions of the mammal's central nervous system to the at least one therapeutic agent as compared with the targeted specific region.

2. The method of claim 1, further comprising allowing a time period to pass after the intranasal administration and delivery of the at least an effective dose of the at least one therapeutic agent to the patient's central nervous system, and before the focusing of ultrasound energy on the specific region within the mammal's central nervous system to drive the effective dose of the therapeutic agent from the perivascular space of the central nervous system into the parenchymal tissue of the targeted specific region.

3. The method of claim 2, wherein the damaged or degenerating or injured central nervous system comprises at least one of the group consisting of: Alzheimer's disease, Parkinson's disease, stroke, narcolepsy, traumatic brain injury, post-traumatic stress disorder (PTSD), amyotrophic lateral sclerosis (ALS), Huntington's disease, spinal cord injury, epilepsy, transient ischemic attacks, hemorrhage, pain, depression, anxiety, schizophrenia, personality disorder, autism, social communication disorder, attention deficit disorder, and an eating disorder.

4. The method of claim 1, wherein the damaged or degenerating or injured central nervous system comprises at least one of the group consisting of: Alzheimer's disease, Parkinson's disease, stroke, narcolepsy, traumatic brain injury, post-traumatic stress disorder (PTSD), amyotrophic lateral sclerosis (ALS), Huntington's disease, spinal cord injury, epilepsy, transient ischemic attacks, hemorrhage, pain, depression, anxiety, schizophrenia, personality disorder, autism, social communication disorder, attention deficit disorder, and an eating disorder.

5. The method of claim 1, further comprising the at least one therapeutic agent comprising at least one metal chelator.

6. The method of claim 1, further comprising the at least one therapeutic agent comprising at least one iron chelator.

7. The method of claim 1, further comprising the at least one therapeutic agent comprising at least one copper chelator.

8. The method of claim 1, further comprising the at least one therapeutic agent comprising insulin.

* * * * *